(12) United States Patent
Abrams

(10) Patent No.: US 9,999,536 B2
(45) Date of Patent: Jun. 19, 2018

(54) OSTOMY BARRIER SEAL

(71) Applicant: Benson Turtleneck Barrier LLC, New York, NY (US)

(72) Inventor: Gilbert L. Abrams, Fort Montgomery, NY (US)

(73) Assignee: Benson Turtleneck Barrier LLC, New York, NY (US)

(*) Notice: Subject to any disclaimer, the term of this patent is extended or adjusted under 35 U.S.C. 154(b) by 168 days.

(21) Appl. No.: 13/902,963

(22) Filed: May 27, 2013

(65) Prior Publication Data

US 2013/0261574 A1    Oct. 3, 2013

Related U.S. Application Data

(63) Continuation-in-part of application No. 13/337,077, filed on Dec. 24, 2011, now Pat. No. 8,449,513.

(60) Provisional application No. 61/460,093, filed on Dec. 27, 2010, provisional application No. 61/463,109, filed on Feb. 14, 2011.

(51) Int. Cl.
*A61F 5/44* (2006.01)
*A61F 5/445* (2006.01)

(52) U.S. Cl.
CPC .......... *A61F 5/4407* (2013.01); *A61F 5/445* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,054,535 A | * | 9/1936 | Diack | A61F 5/445 604/333 |
| 2,327,514 A | * | 8/1943 | Fenwick | A61F 5/445 604/333 |
| 2,502,742 A | * | 4/1950 | Nothdurft | A61F 5/445 604/333 |
| 2,536,036 A | * | 1/1951 | Cloninger | A61F 5/445 604/332 |
| 2,555,086 A | * | 5/1951 | Edwin | A61F 5/445 604/333 |
| 2,616,425 A | * | 11/1952 | Pappas | A61F 5/442 604/277 |
| 2,688,327 A | * | 9/1954 | Samuel | A61F 5/445 604/333 |
| 2,689,567 A | * | 9/1954 | Welch | A61F 5/445 604/277 |
| 2,918,064 A | * | 12/1959 | Booth | A61F 5/442 604/277 |

(Continued)

*Primary Examiner* — Todd J Scherbel
*Assistant Examiner* — Guy K Townsend
(74) *Attorney, Agent, or Firm* — Dara L. Onofrio, Esq.; Onofrio Law

(57) ABSTRACT

An ostomy barrier seal comprising an open-ended conical base 1; and a flange portion 2 extending radially from the base; wherein the conical base 1 has a top opening 3 and a bottom opening 5 for receiving a stoma of a user and the top opening diameter 9 is smaller than the bottom opening diameter 11; such that the stoma of the user fits through the bottom opening and the top opening expands to snuggly fit around and seal along the stoma wall; a related ostomy appliance incorporating the barrier seal; and a related method using the barrier seal to reduce the incidence of waste leakage in an ostomy patients.

22 Claims, 6 Drawing Sheets

(56) References Cited

U.S. PATENT DOCUMENTS

| | | | | |
|---|---|---|---|---|
| 3,507,282 A * | 4/1970 | Burding | A61F 5/445 | 604/333 |
| 3,612,053 A * | 10/1971 | Pratt | A61F 5/445 | 604/338 |
| 3,672,370 A * | 6/1972 | Marsan | A61F 5/442 | 604/277 |
| 3,718,141 A * | 2/1973 | Goetz | A61F 5/445 | 604/333 |
| 4,050,461 A * | 9/1977 | Ruby | A61F 5/442 | 604/277 |
| 4,170,231 A * | 10/1979 | Collins | A61F 5/448 | 131/243 |
| 4,331,148 A * | 5/1982 | Steer | A61F 5/445 | 604/333 |
| 4,387,713 A * | 6/1983 | Calanni | A61F 5/445 | 600/573 |
| 4,620,999 A * | 11/1986 | Holmes | A61F 5/445 | 206/524.3 |
| 4,784,656 A * | 11/1988 | Christian | A61F 5/4408 | 604/332 |
| 4,826,495 A * | 5/1989 | Petersen | A61F 5/441 | 604/333 |
| 5,074,944 A * | 12/1991 | Trenka | B30B 1/00 | 100/237 |
| 5,110,390 A * | 5/1992 | Martini | A61F 5/445 | 156/244.11 |
| 5,348,546 A * | 9/1994 | Norton | A61F 5/445 | 604/332 |
| 5,372,594 A * | 12/1994 | Colacello | A61F 5/441 | 55/385.4 |
| 5,658,266 A * | 8/1997 | Colacello | A61F 5/441 | 604/277 |
| 5,976,118 A * | 11/1999 | Steer | A61F 5/441 | 604/332 |
| 6,007,525 A * | 12/1999 | Martell | A61F 5/445 | 604/333 |
| 6,050,983 A * | 4/2000 | Moore | A61F 5/4405 | 128/DIG. 24 |
| 6,231,553 B1 * | 5/2001 | Hulett | A61F 5/441 | 128/DIG. 24 |
| 6,532,971 B2 * | 3/2003 | Deecki | A61F 5/445 | 134/169 R |
| 6,764,473 B2 * | 7/2004 | Morton | A61F 5/4407 | 604/317 |
| 6,964,654 B2 * | 11/2005 | Fanti | A61F 5/445 | 604/333 |
| 7,160,275 B2 * | 1/2007 | Falconer | A61F 5/441 | 604/333 |
| 7,214,217 B2 * | 5/2007 | Pedersen | A61F 5/441 | 604/332 |
| 7,470,263 B2 * | 12/2008 | Strobech | A61F 5/441 | 604/330 |
| 7,601,143 B2 * | 10/2009 | Eakin | A61F 5/445 | 604/174 |
| 7,699,824 B2 * | 4/2010 | Axelsson | A61F 5/448 | 604/317 |
| 7,737,321 B2 * | 6/2010 | Elliott | A61F 5/445 | 200/61.04 |
| 7,780,641 B2 * | 8/2010 | Ferko | A61F 5/445 | 604/332 |
| 7,815,618 B2 * | 10/2010 | Schena | A61F 5/4407 | 604/332 |
| 7,857,796 B2 * | 12/2010 | Cline | A61F 5/448 | 600/29 |
| 7,879,015 B2 * | 2/2011 | Villefrance | A61F 5/4405 | 604/332 |
| 8,070,737 B2 * | 12/2011 | Cline | A61F 5/445 | 128/887 |
| 8,100,875 B2 * | 1/2012 | Cline | A61F 5/445 | 53/133.6 |
| 8,377,020 B1 * | 2/2013 | Berven | A61F 5/445 | 604/264 |
| 8,764,716 B2 * | 7/2014 | Christensen | A61F 5/4405 | 604/326 |
| 2001/0023337 A1 * | 9/2001 | Lapcevic | A61F 5/4405 | 604/332 |
| 2002/0077611 A1 * | 6/2002 | von Dyck | A61F 5/442 | 604/333 |
| 2003/0014023 A1 * | 1/2003 | Kanbara | A61F 5/441 | 604/333 |
| 2007/0027434 A1 * | 2/2007 | Pedersen | A61F 5/441 | 604/333 |
| 2007/0060900 A1 * | 3/2007 | Maurer | A61F 5/441 | 604/333 |
| 2007/0282284 A1 * | 12/2007 | Mullejans | A61F 5/4404 | 604/333 |
| 2008/0071236 A1 * | 3/2008 | Lee | A61F 5/448 | 604/333 |
| 2008/0154220 A1 * | 6/2008 | Gaffney | A61F 5/445 | 604/333 |
| 2008/0306459 A1 * | 12/2008 | Albrectsen | A61F 5/441 | 604/333 |
| 2009/0069764 A1 * | 3/2009 | Burlot | A61F 5/448 | 604/345 |
| 2009/0163885 A1 * | 6/2009 | Pedersen | A61F 5/448 | 604/333 |
| 2009/0247970 A1 * | 10/2009 | Keleny | A61F 5/441 | 604/333 |
| 2010/0016819 A1 * | 1/2010 | Gill | A61F 5/4405 | 604/333 |
| 2010/0121291 A1 * | 5/2010 | Davies | A61F 5/445 | 604/333 |
| 2011/0196323 A1 * | 8/2011 | Gill | A61F 5/4405 | 604/333 |
| 2012/0172823 A1 * | 7/2012 | Smith | A61F 5/441 | 604/333 |
| 2012/0179124 A1 * | 7/2012 | Nguyen-Demary | A61F 5/445 | 604/333 |
| 2013/0035653 A1 * | 2/2013 | Kannankeril | A61F 5/441 | 604/333 |
| 2013/0060212 A1 * | 3/2013 | Hanuka | A61F 5/445 | 604/333 |
| 2013/0072885 A1 * | 3/2013 | Luther | A61F 5/4404 | 604/333 |
| 2013/0072886 A1 * | 3/2013 | Schertiger | A61F 5/441 | 604/333 |
| 2013/0310782 A1 * | 11/2013 | Chang | A61F 5/441 | 604/333 |
| 2014/0194843 A1 * | 7/2014 | Masters | A61F 5/4405 | 604/333 |
| 2014/0288517 A1 * | 9/2014 | Tsai | A61F 5/445 | 604/333 |
| 2014/0330229 A1 * | 11/2014 | Lee | A61F 5/441 | 604/333 |
| 2014/0371698 A1 * | 12/2014 | Chang | A61F 5/445 | 604/333 |

* cited by examiner

SECTION A-A

OSTOMY BARRIER SEAL

This application is a continuation-in-part of U.S. Ser. No. 13/337,077 filed Dec. 24, 2011, which claims the benefit of U.S. provisional application No. 61/460,093 filed Dec. 27, 2010 and U.S. provisional application No. 61/463,109 filed Feb. 14, 2011, all of which are incorporated herein in their entirety by reference.

FIELD OF THE INVENTION

This invention relates to an ostomy barrier seal that fits snuggly over the stoma of a patient to form a fluid tight seal without glue or adhesives. More particularly, the barrier seal of the invention is an elastomeric material which expands and/or constricts to snuggly fit around and seal along the stoma wall.

BACKGROUND OF THE INVENTION

By definition, ostomy refers to a surgical procedure creating an opening in the body for the discharge of body wastes. Certain diseases of the bowel or urinary tract involve removing all or part of the intestine or bladder. This creates a need for an alternate way for feces or urine to leave the body. An opening is surgically created in the abdomen for body wastes to pass through. The result of the surgical procedure is called an ostomy. The opening that is created at the end of the bowel or ureter is called a stoma, which is pulled through the abdominal wall. The size of a stoma depends on the individual as well as the organ it was made from. Stomas are of various widths and heights (from the abdominal wall). As used in the specification herein the segment that is outside the abdomen is referred to as the stoma wall.

Different types of ostomy are performed depending on how much and what part of the intestines or bladder is removed.

The three most common types of ostomies are:
1. colostomy;
2. ileostomy; and
3. urostomy.

A colostomy is a when a small portion of the colon (large intestine) is brought to the surface of the abdominal wall to allow stool to be eliminated. A colostomy may be temporary or permanent. A permanent colostomy usually involves the loss of the rectum. A colostomy might be performed due to cancer, diverticulitis, colitis, imperforate anus, Hirschsprung's disease, or trauma to the affected area.

An ileostomy is an opening created in the small intestine to bypass the colon for stool elimination. The end of the ileum, which is the lowest part of the small intestine, is brought through the abdominal wall to form a stoma. An ileostomy might be performed due to ulcerative colitis, Crohn's disease, or familial polyposis.

A urostomy is a surgical procedure that diverts urine away from a diseased or defective bladder. Among several methods to create the urostomy, the most common methods are called an ileal or large intestinal conduit. Either a section at the end of the small intestine (ileum) or a section of the large intestine is isolated from the fecal stream and relocated surgically to form a stoma for urine to pass out of the body. Other common names for this procedure are ileal loop or colon conduit. A urostomy may be performed due to bladder cancer, spinal cord injuries, malfunction of the bladder, and birth defects such as spina bifida.

Since colostomy, ileostomy, and urostomy bypass the sphincter muscle there is no voluntary control over bowel movements or urination and an external pouch must be worn to catch the discharge.

The skin around the stoma, called the peristomal skin, must be protected from direct contact with discharge. The discharge can be irritating to the stoma since it is very high in digestive enzymes or urinary products. The peristomal skin should be cleansed with plain soap and rinsed with water at each change of the pouch.

The stoma can change in size due to weight gain/loss or several other determining factors. To ensure proper fit of the discharge pouch conventional practice dictates the stoma should be measured each time supplies are purchased.

People with ostomies can be prone to certain types of skin infections. Skin irritations or rashes around the stoma may be caused by leakage due to an improperly fitted (cemented) barrier seal. Correctly fitting the barrier and carefully cleaning the skin around the stoma after each change are the best ways of preventing skin irritation.

Conventional pouching systems include a one-piece or two-piece system. Both kinds include a skin barrier/wafer ("faceplate" in older terminology) and a collection pouch. The pouch (one-piece or two-piece) attaches to the abdomen by the skin barrier and is fitted over and around the stoma to collect the diverted output, either stool or urine. The barrier/wafer is designed to protect the skin from the stoma output and to be as neutral to the skin as possible.

Colostomy and Ileostomy pouches are either open-ended, requiring a closing device (traditionally a clamp or tail clip); or closed and sealed at the bottom. Open-ended pouches are called drainable and are left attached to the body while emptying. Closed end pouches are most commonly used by patients who can irrigate or by patients who have regular elimination patterns. Closed end pouches are usually discarded after one use.

Typically, two piece systems allow changing pouches while leaving the barrier/wafer attached to the skin. The wafer/barrier is part of a "flange" unit. The pouches utilize multiple methods to attach mechanically to a mating piece on the flange. A common connection mechanism consists of a pressure fit snap ring, similar to that used in Tupperware™.

One-piece systems consist of a skin barrier/wafer and pouch joined together as a single unit. These provide greater simplicity than two-piece systems but require changing the entire unit, including skin barrier, when the pouch is changed.

Both two-piece and one-piece pouches can be either drainable or closed.

A typical ostomy barrier is essentially a large adhesive patch, generally 4"×4", with a center hole which varies in size relative to the outer diameter of the stoma, typically ranging from ¼" to 3" diameter center hole. The center hole diameter sizes are either fixed or cut to size by the user. The barrier is three layers thick, with a cloth face, a heavy 3" ring of thick adhesive and a sheet of plastic approximately ¹⁄₆₄" thick. After application, the barrier is expected to remain on the body from 3 to 5 days.

Current barrier seals require that the patient cut the ring in the center of the barrier to a size that fits his or her stoma. This often leaves a jagged edge on the seal, which irritates the stoma causing pain, irritation and bleeding. The invention ostomy barrier seal requires no cutting. It is flexible and automatically sizes, shapes and seal itself along the stoma wall and causes no discomfort.

Further, currently known ostomy barriers require an adhesive glue to make the barrier adhere tightly to the skin around the stoma wall and prevent leakage. U.S. Patent Publication 2011/0172619A1 to Argent describes a device for use with an ostomy appliance that has an opening surrounded by a cylindrical peripheral wall with a flange part. The device is made of a polyurethane material known as Alphathane™ and is said to be elastically deformable. The Argent device comes in various sizes depending on the size of the user's stoma, however, it does not take into account movement and changes in the stoma which depending on activity changes the stoma height and width. The Argent device fails to accommodate these changes thus increasing the incidence of leakage of waste.

One of the major issues with current barriers is that body waste leaks under the barrier glue, irritating the skin close to the stoma and under the adhesives. This causes the adhesive to weaken creating further leakage of body waste allowing the whole barrier to loosen. This can cause spillage and accidents.

The invention overcomes these obstacles by sealing itself around the stoma wall without the use of any further glue, adhesive or scissor cutting. The invention is self-aligning, flexible with stoma movement and much more comfortable to wear than any known device. It fits the stoma in a manner similar to a turtleneck.

The invention provides a more secure fit around the stoma eliminating the need for glue/adhesive currently required (and the resulting skin irritation experienced) when using existing ostomy barriers. It is well known that it is difficult for ostomy patients, after a wearing period, to remove all the glue from the skin around the stoma. Soap and water and light scrubbing on the skin is necessary. This is not only time consuming but is irritating and causes ongoing sensitivity in the area as well as discomfort. All the glue must be removed completely from the skin before new application of the glue and a new barrier applied. The invention overcomes these disadvantages by eliminating the need for any glue/adhesives and provides a mechanical, more comfortable seal.

The invention is more convenient to use than current products on the market. In most cases, ostomy patients require a mirror to enable them to see where the stoma is for positioning the barrier. Most public restrooms do not provide shelves to place supplies and a mirror while applying or removing barriers in privacy. If leakage occurs while patients are outside the home, most patients are embarrassed and feel pressured to return home to address the problem. The ease of application and self-fitting nature of the invention barrier seal facilitates greater peace of mind, mobility and flexibility in patient's going about their daily activities.

Advantage of the present invention device and related method and system is in the provision of an ostomy barrier seal that provides a flexible, self-adjusting seal to compensate for out of round, height center line and angular variants of stomas. The invention functions as a mechanical seal providing better protection against leakage and prevents irritation of the stoma and surrounding skin than the glue affixed to current barriers in the market. The invention is more comfortable and a more convenient solution than what is currently available.

The invention provides a soft seal around the stoma of the individual and takes into account variations within a number of sizes and allows for easy application. It eliminates the need for additional accessory products and makes for a more comfortable and secure fit on the user.

The invention eliminates the conventional method of scissor cutting a hole in the barrier to fit the stoma, as well as the elimination of cement, permitting a faster installation of the barrier. The self-aligning feature makes the use of a sight mirror unnecessary.

A general object of the invention is to provide an ostomy barrier seal that is a flexible, self-adjusting seal adapted to fit around a user's stoma without the need for any adhesive or other cement to ensure a sufficient seal. The barrier seal is made of flexible material, includes an opening to allow protrusion of the stoma, and is attached to a barrier. In an alternate embodiment the ostomy barrier seal may be attached directly to the user's skin.

The invention barrier seal may be used with conventional barriers which comprise a cloth or woven backing with an adhesive applied to the body side. Both the body side and the pouch side of the barrier are substantially flat. A plastic ring for coupling to an ostomy bag is located on the pouch side of the barrier and surrounds the outer periphery of the flexible, self-adjusting barrier seal.

An object of the invention is its easy placement on the user without using a mirror.

Yet another object of the invention is that it eliminates the need for glue around the stoma which not only irritates the stoma and skin, but must be removed and reapplied after each application.

Another object of the invention is to properly place a barrier device on ostomy patients which prevents irritation and bleeding.

Yet another object of the invention is to provide a translucent plastic material barrier seal which permits visual confirmation of the seal along the stoma wall.

A further object of the invention is its self-aligning and continual sealing ability to accommodate stoma movement.

Another object of the invention is its comfort to the user in the elimination of pressure and discomfort.

Another object of the invention is in the reduction of the number of sizes required to accommodate different stoma widths.

SUMMARY OF THE INVENTION

The present invention provides an ostomy barrier seal comprising an open-ended conical base and a flange portion extending radially from the base. The conical base has a top opening and a bottom opening for receiving a stoma of a user, wherein the top opening diameter is smaller than the bottom opening diameter. The stoma of the user fits through the bottom and top openings. Since the top opening is smaller than the bottom it expands to snuggly fit around and seal along the stoma wall, thus preventing leakage of waste.

The barrier seal of the invention comprises a thermoplastic elastomer capable of stretching without breaking. Preferably the thermoplastic elastomer is a styrene block copolymer, most preferably a styrene-butadiene-styrene block copolymer.

In one embodiment of the invention, the top opening diameter is no less than 20% of the bottom opening diameter. Typically the top opening diameter has a diameter between 20-80% of the bottom opening diameter, more preferably between 25-75%, and most preferably between 25-40%.

The bottom opening preferably has a diameter in a range between ¼" to 3" to accommodate all stoma widths. A ursotomy typically would only have a diameter in the range between ¼" to ½". These ranges are not meant to be limiting in any way and other sizes outside this range are included as part of the invention.

The conical base has a height that is dependent on the diameter of the top opening diameter. The smaller the top opening diameter is the higher the conical base. The larger the top opening diameter is the shorter the conical base.

The barrier seal of the invention is constructed in order to create the proper contact pressure to create a seal along the stoma wall. It fits the stoma in a manner similar to a turtleneck. The interior angle between the conical base and the flange is preferably between 20 to 40 degrees, most preferably between 25 to 35 degrees.

The flange portion may further include a locking mechanism on the underside surface for attaching to an ostomy barrier, including but not limited to use for colostomies, ileostomies and urostomies.

In another embodiment, the barrier seal includes at least one bellow between the base and the flange portion. While the barrier seal itself is flexible the bellow permits normal movement and expansion of the stoma without interfering with the seal itself along the stoma wall.

The underside of the flange has an adhesive surface. Conventional adhesives can be used in the invention. This adhesive surface can attach the barrier seal to the user's skin, an ostomy barrier or an ostomy pouching device.

In another embodiment, preferably for short stomas or sub-dermal stomas, the ostomy barrier seal has an open-ended base with a top edge that forms a top opening and a bottom edge that forms a bottom opening for receiving a stoma of a user. The bottom opening diameter is smaller than the top opening diameter. This embodiment includes at least one bellow portion that extends radially from the bottom edge; and a flange portion that extends radially from the bellow. The invention seal is pressed down over the stoma of the user and fits through the top opening and bottom opening wherein the bottom opening snuggly fits around and seals along the stoma wall.

This embodiment is the inverse of the embodiment described earlier since the bottom opening is smaller than the top and is for use with a short or sub-dermal stoma. The addition of a bellows permits the invention barrier seal to adjust the pressure on the stoma to maintain uniform contact during normal activity of the stoma and to keep a tight seal.

The invention also provides an ostomy appliance including a barrier seal. The barrier seal includes an open-ended base having a first opening and a second opening at opposite ends of the base for receiving the stoma of a user. The first opening and second opening are different diameters with a flange portion extending radially from the second opening. This barrier seal is attached to a barrier to form the ostomy appliance.

In one embodiment of the ostomy appliance the first opening diameter is smaller than the second opening diameter, such that the stoma of the user fits through the second opening; and the first opening expands to snuggly fit around and seal along the stoma wall.

In another embodiment of the ostomy appliance the second opening diameter is smaller than the first opening diameter. The stoma of the user easily fits through the first opening and the second opening expands and then constricts around the stoma wall to form a fluid tight seal. In both these embodiments the barrier seal may further include at least one bellow between the second opening and the flange portion.

The ostomy appliance may further include an ostomy pouch which is attached to the barrier.

The invention also includes a method to reduce the incidence of waste leakage in ostomy patients. This is accomplished by providing an ostomy barrier seal comprising an open-ended conical base and a flange portion extending radially from the base and attaching the barrier seal to a barrier. The barrier is applied over the stoma of a patient such that the barrier seal fits snuggly over the stoma without glue or adhesive to form a fluid tight seal along the stoma wall. An ostomy pouch is attached to the barrier; wherein the barrier seal reduces and prevents waste leakage.

In a preferred embodiment the conical base of the barrier seal has a top opening and a bottom opening, wherein the top opening diameter is smaller than the bottom opening diameter; such that the stoma of the user fits through the bottom opening and the top opening expands to snuggly fit around and seal along the stoma wall.

In another preferred embodiment the conical base of the barrier seal has a top opening and a bottom opening for receiving a stoma of a user, wherein the bottom opening diameter is smaller than the top opening diameter. The barrier seal also includes at least one bellows portion between the bottom opening and the flange portion such that the stoma of the user fits through the top opening and the bottom opening expands and constricts to fit around and seal along the stoma wall. The barrier seal is preferably made of a thermoplastic elastomer capable of stretching.

Other objects, features and advantages of the present invention will be apparent when the detailed description of the preferred embodiments of the invention are considered with reference to the drawings, which should be construed in an illustrative and not limiting sense.

BRIEF DESCRIPTION OF THE DRAWINGS

FIG. 1A is a top view of the barrier seal; FIG. 1B is a cross-section of the barrier seal with an adhesive surface and FIG. 1C is a cross section of the barrier seal with a locking mechanism to attach to a barrier;

FIG. 3A is a top view of the barrier seal and FIG. 3B is a cross-section of the barrier seal;

FIG. 4A shows the ostomy barrier seal with one bellow; FIG. 4B shows the ostomy barrier seal with two bellows; and FIG. 4C is a schematic illustration showing the top view of the different size stomas that can be accommodated by the invention; the dotted line represents the center axis throughout the three illustrations;

FIG. 6A is a top view of the barrier seal; FIG. 6B is a top view cross-section of the barrier seal; and FIG. 6C is a side cross section of the barrier; FIG. 7A shows the barrier seal 10 and barrier 13 separately; FIG. 7B shows the assembled barrier and barrier seal illustrating a cross section A-A of the barrier seal opening; and FIG. 7C shows the assembled barrier with the invention barrier seal.

DETAILED DESCRIPTION OF THE INVENTION

Figure 1A:
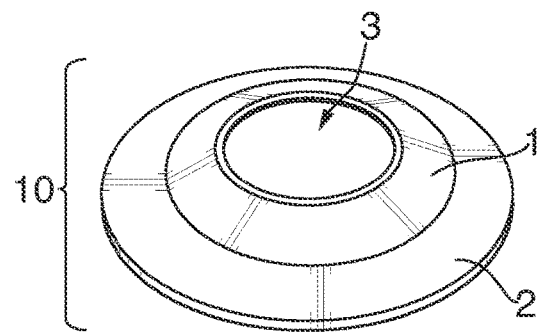
FIGS. 1A-1C illustrate the ostomy barrier seal of the invention.

In order to understand the invention and to see how it may be carried out in practice, the preferred embodiments will now be described, by way of non-limiting example only, with reference to the drawings.

As used in the specification herein the terms ostomy and stoma are general descriptive terms that are often used interchangeably though they have different meanings. As mentioned earlier, ostomy refers to the surgically created opening in the body for the discharge of body wastes and a stoma is the actual end of the ureter or small or large bowel that can be seen protruding through the abdominal wall.

The barrier seal of the invention is referred to as an "ostomy" barrier seal and is meant to encompass all stomas created by surgical procedures, including but not limited to colostomy; ileostomy; and urostomy and variations therein.

As used in the figures the drawing reference numerals are as follows
1 Open ended conical base;
2 Flange portion;
3 Top opening;
4 Adhesive surface;
5 Bottom opening;
6 Top edge;
7 Bottom edge;
8 Locking mechanism (locating ring);
9 Top opening diameter;
10 Ostomy barrier seal;
11 Bottom opening diameter;
12 Bellow;
13 Barrier;
15 Stoma;
20 Ostomy barrier seal (another embodiment);
21 First opening diameter;
22 Second opening diameter.

Figure 1B:
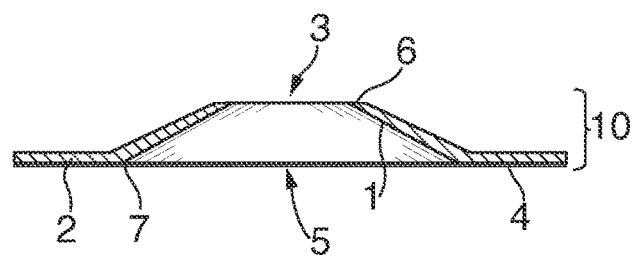
Figure 1C:
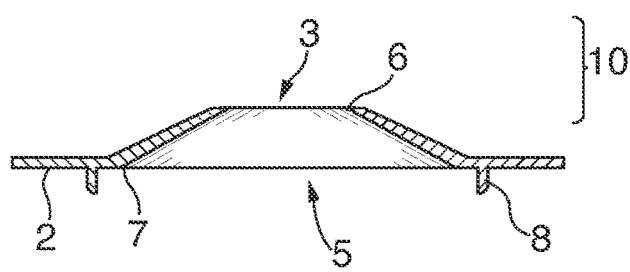
Figure 2:
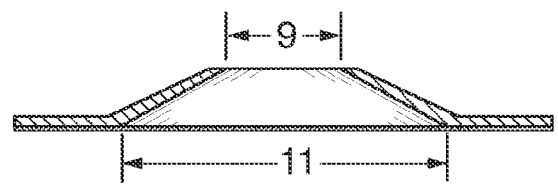
FIG. 2 is a cross section of the ostomy barrier seal of the invention illustrating the top opening diameter and the bottom opening diameter.

FIGS. 1A to 1C illustrate the ostomy barrier seal of the invention. In general, FIG. 1A illustrates the top view of the barrier seal of the invention. The ostomy barrier seal comprises an open-ended conical base 1; and a flange portion 2 extending radially from the base.

FIG. 1B is a cross-section of the barrier seal with an adhesive surface. As illustrated the conical base 1 of the barrier seal has a top opening 3 and a bottom opening 5 for receiving a stoma of a user, wherein the top opening diameter 9 is smaller than the bottom opening diameter 11. The barrier seal is of uniform thickness. In this embodiment the bottom opening is essentially fixed and fits the width of the user's stoma. The top opening of the barrier seal is smaller than the stoma width thus the device is able to accommodate varying stoma sizes. When ready to be used the stoma of the user easily fits through the bottom opening and the top opening expands to fit around and seal along the stoma wall. The invention device fits the stoma in a manner similar to a turtleneck.

The underside of the flange has an adhesive surface 4. Conventional adhesives may be used in the invention. In one embodiment the adhesive surface 4 attaches to the users skin. In an alternate embodiment the adhesive surface 4 attaches to an ostomy barrier. In yet another embodiment the adhesive surface 4 attaches to an ostomy pouching device.

The barrier seal according to the invention is preferably made of a thermoplastic elastomer. In preferred embodiments, the thermoplastic elastomer is a styrene block copolymer and in most preferred embodiments the thermoplastic elastomer is a styrene-butadiene-styrene block copolymer. Thermoplastic elastomer's known as Dynaflex™ (commercially available from PolyOne Corporation, Avon Lake, Ohio) are preferred materials used in the invention because of their key characteristics. The technical data sheets of Dynaflex™ are incorporated herein by reference. The materials have a tactile feel and ultra soft touch enhancing the comfort to the user when used in the invention barrier seal. The material used in the invention is extremely elastic and strong. The tensile strength (break 73° F./23° C.) range from 220 psi to 550 psi and tensile elongation (break 73° F./23° C.) range from 650% to 1110%. The Durometer Hardness values for the materials used are up to 20 S (as measured by ASTM D2240—Shore A, 10 sec), most preferably in the range from 3-14. The material is also translucent which permits the user to visually see that the barrier is sealed along the stoma wall. While Dynaflex™ is described as a preferred material any material having similar characteristics can be used in the invention.

In one embodiment of the invention, the top opening diameter is no less than 20% of the bottom opening diameter. Typically the top opening diameter has a diameter between 20-80% of the bottom opening diameter, more preferably between 25-75%, and most preferably between 25-40%.

The bottom opening preferably has a diameter in a range between ¼" to 3" to accommodate all stoma widths. A ursotomy typically would only have a diameter in the range between ¼" to ½". These ranges are not meant to be limiting in any way and other sizes outside this range are included as part of the invention.

The conical base has a height that is dependent on the diameter of the top opening diameter. The smaller the top opening diameter is the higher the conical base. The larger the top opening diameter is the shorter the conical base.

The barrier seal of the invention is constructed in order to create the proper contact pressure to create a seal along the stoma wall. It fits the stoma in a manner similar to a turtleneck. The interior angle between the conical base and the flange is preferably between 20 to 40 degrees, most preferably between 25 to 35 degrees.

The barrier seal according to the invention can further include a locking mechanism. The flange portion 2 may include a locking mechanism 8 on the underside surface for attachment to an ostomy barrier, including but not limited to use for colostomies, ileostomies and urostomies. FIG. 1C is a cross section of the barrier seal with a locking mechanism to attach to a barrier.

Figure 3A:
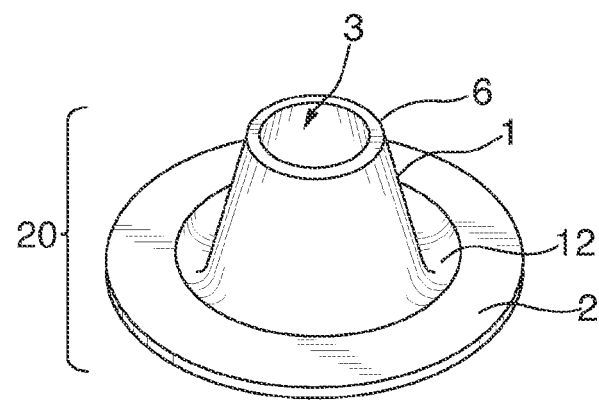
FIGS. 3A-3B illustrates the ostomy barrier seal of the invention with a bellow.
Figure 3B:
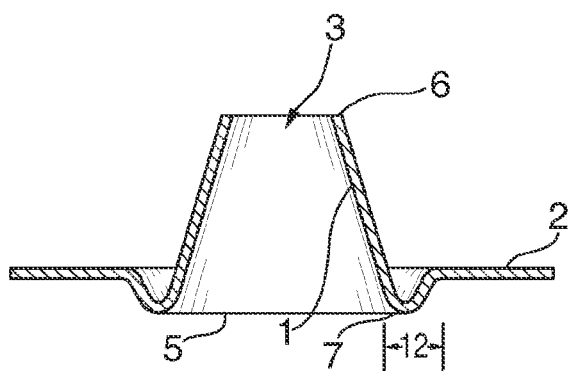

FIGS. 3A-3B illustrates the ostomy barrier seal of the invention with a bellow. FIG. 3A is a top view of the barrier seal and FIG. 3B is a cross-section of the barrier seal. As shown the barrier seal comprises at least one bellow 12 between the base 7 and the flange portion 2.

Figure 4A:
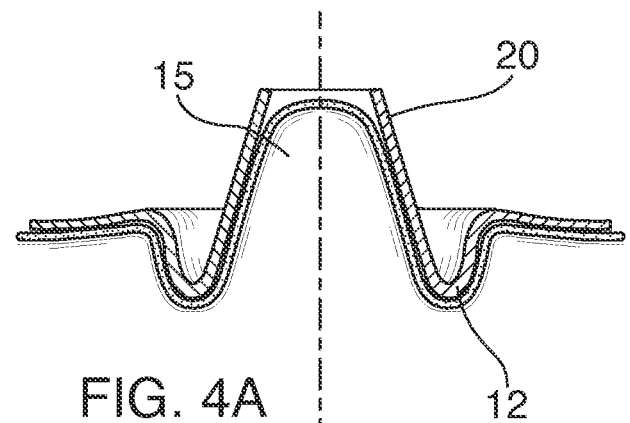
FIGS. 4A-4C illustrate how a stoma is inserted into a barrier seal according to the invention.
Figure 4B:
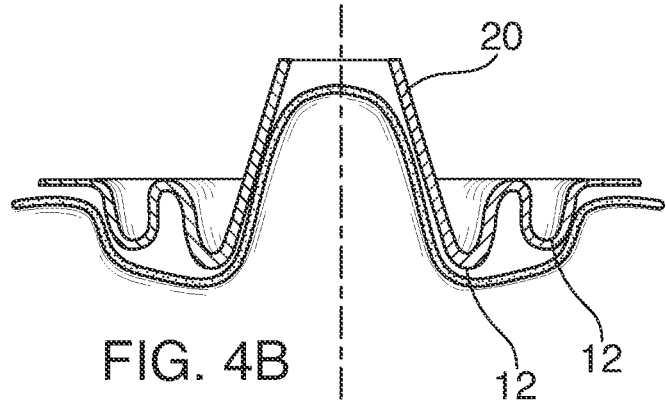
Figure 4C:
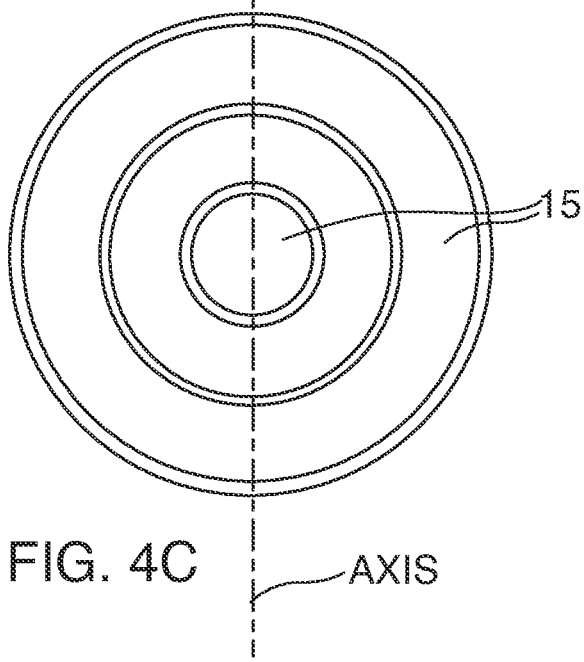

FIGS. 4A-4C illustrates how a stoma is inserted into a barrier seal according to the invention. FIG. 4A shows the ostomy barrier seal with one bellow 12. The bellow permits the seal to move with the stoma and accommodates for movements, changes in height and width of the stoma without breaking the seal along the stoma wall. The bellow 12 also assists the user in placement of the barrier seal over the stoma.

FIG. 4B shows the ostomy barrier seal with two bellows 12.

FIG. 4C is a schematic illustration showing the top view of the different size stomas 15 that can be accommodated by the invention. The dotted line represents the center axis throughout the three illustrations and schematically shows that the barrier seal of the invention accommodates various size stoma widths. The barrier seal of the invention accommodates a large variety of stoma sizes due to the elasticity of the material used.

Figure 5:
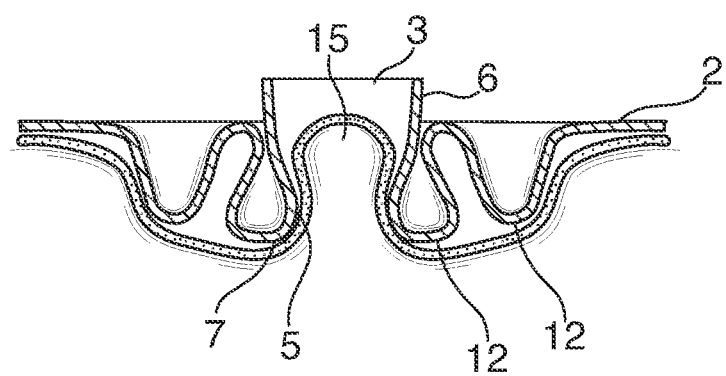
FIG. 5 is another embodiment of the ostomy barrier seal of the invention which is preferably used in a patient with a short stoma or sub-dermal stoma; the bottom opening is smaller than the top opening and two bellows are present (although one bellow is also acceptable)

FIG. 5 is another embodiment of the ostomy barrier seal of the invention which is preferably used in a patient with a short stoma or sub-dermal stoma. The bottom opening is smaller than the top opening. The figure shows two bellows 12 are present although one bellow is also acceptable and in accordance with the invention.

As shown in FIG. 5 an ostomy barrier seal is provided having an open-ended base 1 having a top edge 6 which forms a top opening 3 and a bottom edge 7 which forms a bottom opening 5 for receiving a stoma of a user. The bottom opening diameter is smaller than the top opening diameter and at least one bellow portion 12 is present extending radially from the bottom edge. The flange portion 2 extending radially from the bellow 12; such that the stoma of the user fits through the top opening and the bottom opening wherein the bottom opening snuggly fits around and seals along the stoma wall. Since a short stoma or sub-dermal stoma is sometimes difficult to secure to a barrier, this embodiment improves and enhances the sealing of a short stoma or sub-dermal stoma to reduce and prevent leakage of waste.

When ready for use the invention seal is pressed down over the stoma of the user and fits through the top opening. The bottom opening expands and then constricts so that the bottom opening snuggly fits around and seals along the stoma wall.

This embodiment is the inverse of the embodiment described earlier since the bottom opening is smaller than the top and is for use with a short or sub-dermal stoma. The addition of a bellows permits the invention barrier seal to adjust the pressure on the stoma to maintain uniform contact during normal activity of the stoma and to keep a tight seal.

As in the earlier described embodiments the barrier seal of the invention is constructed in order to create the proper contact pressure to create a seal along the stoma wall. However, since this embodiment is the inverse, the outside angle between the bottom opening and either the flange or the bellow (depending on whether the bellow is present) is preferably between 20 to 40 degrees, most preferably between 25 to 35 degrees.

Figure 6A:
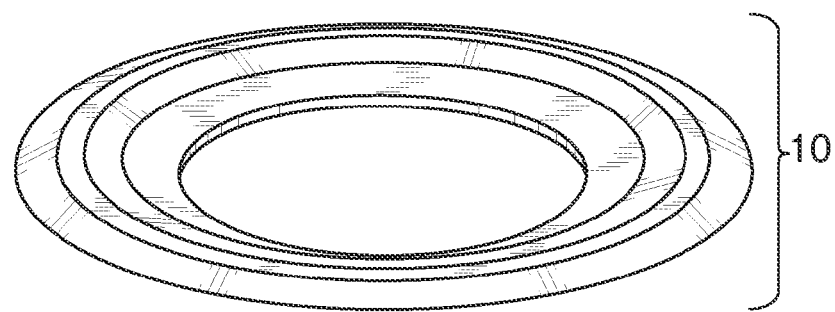
FIGS. 6A-6C illustrate a shallow barrier seal according to the invention.
Figure 6B:
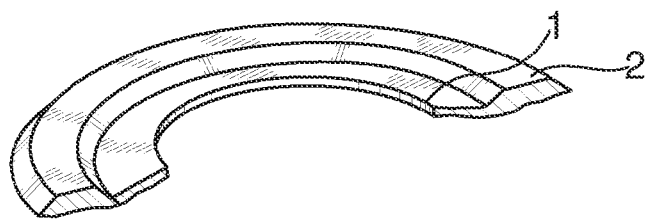
Figure 6C:
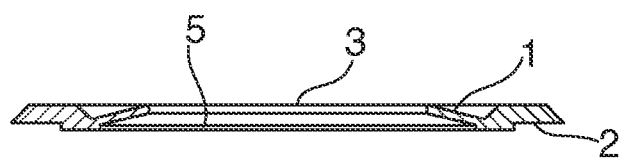

FIGS. 6A-6C illustrates a shallow barrier seal 10 according to the invention. FIG. 6A is a top view of the barrier seal. FIG. 6B is a top view cross-section of the barrier seal. FIG. 6C is a side cross section of the shallow barrier seal. As described, the conical base has a height that is dependent on the diameter of the top opening diameter. The smaller the top opening diameter is the higher the conical base. The larger the top opening diameter is the shorter the conical base. These figures illustrate the invention barrier 10, wherein the height of the conical base 1 is shallow. As illustrated in FIG. 3, the top opening 3 of the device relative to the bottom opening 5 creates a shallow or short conical base 1 height. In keeping with the invention, the angle between the conical base and the flange 2 is between 20 to 40 degrees, most preferably between 25 to 35 degrees.

Figure 7A:
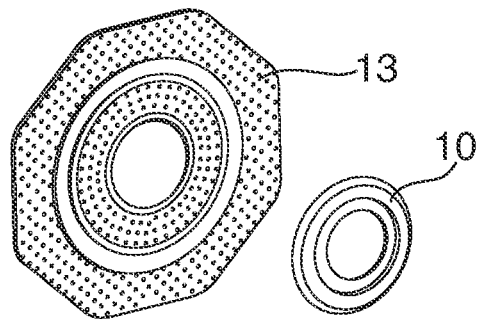
FIGS. 7A-7C illustrate the barrier seal 10 according to the invention assembled to an ostomy barrier.
Figure 7B:
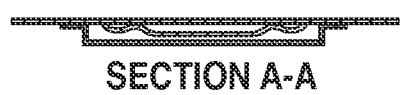
Figure 7B:
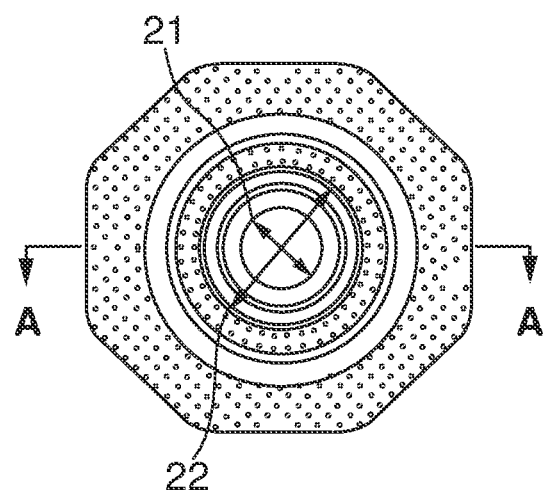
Figure 7C:
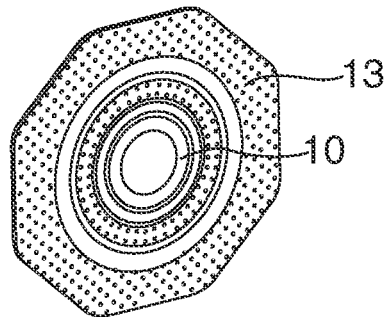

FIGS. 7A-7C illustrates the barrier seal 10 according to the invention assembled to an ostomy barrier. FIG. 7A shows the barrier seal 10 and barrier 13 separately. FIG. 7B shows the assembled barrier and barrier seal indicating a cross section A-A of the barrier seal opening. FIG. 7C shows the assembled barrier with barrier seal.

As shown in FIG. 7B an ostomy appliance is provided made of a barrier seal including an open-ended base 1 having a first opening 21 and a second opening 22 at opposite ends of the base for receiving the stoma of a user. The first opening and the second opening are different diameters. A flange portion 2 extends radially from the second opening. The barrier seal is attached to a barrier to form the ostomy appliance.

In an alternate embodiment the ostomy appliance according to the invention, the first opening diameter is smaller than the second opening diameter, such that the stoma of the user fits through the second opening; and the first opening expands to fit snuggly around the stoma and seal along the stoma wall to prevent leakage.

In yet another embodiment of the ostomy appliance according to the invention the second opening diameter is smaller than the first opening diameter, such that the stoma of the user fits through the first opening and the second opening expands and constricts to fit snuggly around the stoma and seal along the stoma wall to prevent leakage. In both these embodiments the barrier seal may further include at least one bellow between the second opening and the flange portion.

In both embodiments the ostomy appliance includes an ostomy pouch. The ostomy pouch is then attached to the barrier.

The invention also provides a method to reduce the incidence of waste leakage in an ostomy patient. The steps include providing an ostomy barrier seal comprising an open-ended conical base and a flange portion extending radially from the base. A barrier is attached to the barrier seal. The barrier is applied over the stoma of a patient such that said barrier seal fits snuggly around the stoma wall without glue or adhesive to form a fluid tight seal along the stoma wall. An ostomy pouch is attached to the barrier. The barrier seal reduces and prevents waste leakage.

In an alternate embodiment the conical base of the barrier seal has a top opening and a bottom opening, wherein the top opening diameter is smaller than the bottom opening diameter; such that the stoma of the user fits through the bottom opening and the top opening expands to snuggly fit around and seal along the stoma wall.

In yet another embodiment, the conical base of the barrier seal has a top opening and a bottom opening for receiving a stoma of a user, wherein the bottom opening diameter is smaller than the top opening diameter.

The barrier seal further includes at least one bellows portion between the bottom opening and the flange portion; such that the stoma of the user fits through the top opening and the bottom opening expands and constricts to snuggly fit around and seal along the stoma wall.

In all embodiments the barrier seal is made of a thermoplastic elastomer capable of stretching without losing its elasticity. The seal is also translucent which permits the user to visually check the seal around the stoma.

The foregoing description of various and preferred embodiments of the present invention has been provided for purposes of illustration only, and it is understood that numerous modifications, variations and alterations may be made without departing from the scope and spirit of the invention as set forth in the following claims.

The invention claimed is:

1. An ostomy barrier seal comprising:
   an open-ended conical base (1) having a uniform thickness; and
   a flange portion (2) extending radially from said base; wherein said conical base and said flange portion consist essentially of a single thermoplastic elastomer that is strong and elastic and has a hardness value between 3 to 14 S;

wherein said conical base (1) has a top opening (3) and a bottom opening (5) for receiving a stoma of a user, wherein the top opening diameter (9) is between 20 to 80% smaller than the bottom opening diameter (11) and the interior angle between said conical base and said flange is between 20 to 40 degrees;

such that the stoma of the user fits through said bottom opening and said top opening expands and constricts to snuggly fit around and seals along the stoma wall without the use of adhesives or glues; wherein the barrier seal is flexible, self-aligning and has continuous sealing ability to accommodate stoma movement.

2. The barrier seal according to claim 1, wherein said thermoplastic elastomer is a styrene block copolymer.

3. The barrier seal according to claim 1, wherein said thermoplastic elastomer is a styrene-butadiene-styrene block copolymer.

4. The barrier seal according to claim 1, wherein said bottom opening diameter (11) has a range between ¼" to 3".

5. The barrier seal according to claim 1, wherein conical base (1) has a height that is dependent on the diameter of said top opening diameter, such that the smaller said top opening diameter the higher said conical base.

6. The barrier seal according to claim 1 wherein conical base (1) has a height that is dependent on the diameter of said top opening diameter, such that the larger said top opening diameter the shorter said conical base.

7. The barrier seal according to claim 1, wherein said flange portion (2) further comprises a locking mechanism (8) on the underside surface.

8. The barrier seal according to claim 7, wherein said locking mechanism (8) attaches to an ostomy barrier.

9. The barrier seal according to claim 1, further comprising at least one bellow (12) between said base (7) and said flange portion (2).

10. The barrier seal according to claim 1, wherein the underside of said flange has an adhesive surface (4).

11. The barrier seal according to claim 10, wherein said adhesive surface (4) attaches to the users skin.

12. The barrier seal according to claim 10, wherein said adhesive surface (4) attaches to an ostomy barrier.

13. The barrier seal according to claim 10, wherein said adhesive surface (4) attaches to an ostomy pouching device.

14. An ostomy barrier seal comprising:
an open-ended base (1) having a top edge (6) which forms a top opening (3) and a bottom edge (7) which forms a bottom opening (5) for receiving a stoma of a user, wherein the bottom opening diameter is smaller than the top opening diameter; wherein the open-ended base (1) from said top edge (6) to said bottom edge (7) is a uniform thickness;
at least one bellow portion (12) extending radially from said bottom edge, wherein the outside angle between the bottom opening and the bellow is between 20 to 40 degrees; and
a flange portion extending radially from said bellow;
wherein said open-ended base consisting essentially of a thermoplastic elastomer that is strong and elastic and has a hardness value between 3 to 14 S;
such that the stoma of the user fits through said top opening and said bottom opening wherein said bottom opening expands and constricts to snuggly fit around and seal along the stoma wall without the use of adhesives or glues.

15. An ostomy appliance comprised of:
a barrier seal including an open-ended base (1) having a first opening (21) and a second opening (22) at opposite ends of the base for receiving the stoma of a user, wherein said first opening and said second opening are different diameters;
a flange portion (2) extending radially from said second opening; and
a barrier; wherein said open-ended base (1) from the first opening (21) to the second opening (22) is a uniform thickness, and consists essentially of a single thermoplastic elastomer that is strong and elastic and has a hardness value between 3 to 14 S; such that the stoma of the user fits through said first and second openings and expands and constricts to snuggly fit around and seal along the stoma wall.

16. The ostomy appliance according to claim 15, wherein the first opening diameter is smaller than the second opening diameter, such that the stoma of the user fits through said second opening; and said first opening expands to snuggly fit around and seal along the stoma wall.

17. The ostomy appliance according to claim 15, wherein said second opening diameter is smaller than said first opening diameter, such that the stoma of the user fits through said first opening and said second opening expands and constricts to snuggly fit around and seal along the stoma wall.

18. The ostomy appliance according to claim 15, further comprising an ostomy pouch; wherein said ostomy pouch is attached to said barrier.

19. A method to reduce the incidence of waste leakage in an ostomy patient comprising the steps of:
providing an ostomy barrier seal comprising an open-ended conical base having a top opening and a bottom opening of different diameters at opposite ends of the base for receiving the stoma of a user, wherein the conical base from the top opening to the bottom opening is a uniform thickness; and a flange portion extending radially from said base; wherein said open-ended base consists essentially of a thermoplastic elastomer having a hardness value between 3 to 14 S;
attaching said barrier seal to a barrier;
applying said barrier over the stoma of a patient such that said barrier seal expands and constricts to fit snuggly over the stoma and without glue or adhesive forms a fluid tight seal along the stoma wall; and
attaching an ostomy pouch to said barrier; wherein said barrier seal reduces and prevents waste leakage; wherein the barrier seal is flexible, self-aligning and has continuous sealing ability to accommodate stoma movement.

20. The method according to claim 19, wherein the top opening diameter is smaller than the bottom opening diameter; such that the stoma of the user fits through said bottom opening and said top opening expands to snuggly fit around and seal along the stoma wall.

21. The method according to claim 19, wherein the bottom opening diameter is smaller than the top opening diameter.

22. The method according to claim 21, wherein said barrier seal further comprises at least one bellows portion between said bottom opening and said flange portion; such that the stoma of the user fits through said top opening and said bottom opening expands and constricts to snuggly fit around and seal along the stoma wall.

* * * * *